(12) United States Patent
Wiederin et al.

(10) Patent No.: US 7,201,072 B1
(45) Date of Patent: Apr. 10, 2007

(54) AUTOMATED SAMPLING DEVICE

(75) Inventors: Dan Wiederin, Omaha, NE (US); David Diaz, Omaha, NE (US); Gary Barrett, Omaha, NE (US)

(73) Assignee: Elemental Scientific Inc., Omaha, NE (US)

( * ) Notice: Subject to any disclaimer, the term of this patent is extended or adjusted under 35 U.S.C. 154(b) by 0 days.

(21) Appl. No.: 10/966,888

(22) Filed: Oct. 15, 2004

Related U.S. Application Data

(60) Provisional application No. 60/604,548, filed on Aug. 26, 2004.

(51) Int. Cl.
*G01N 1/00* (2006.01)

(52) U.S. Cl. .................................... 73/864.25

(58) Field of Classification Search ............. 73/863.32, 73/864.11, 864.12, 864.21, 864.22, 864.23, 73/864.24, 864.25; 422/63, 100
See application file for complete search history.

(56) References Cited

U.S. PATENT DOCUMENTS

| | | | | |
|---|---|---|---|---|
| 4,311,667 A | * | 1/1982 | Gocho | 422/64 |
| 4,841,786 A | * | 6/1989 | Schulz | 73/864.25 |
| 5,270,211 A | | 12/1993 | Kelln et al. | 436/43 |
| 5,331,840 A | | 7/1994 | Williams | 73/19.1 |
| 5,479,969 A | | 1/1996 | Hardie et al. | 141/130 |
| 5,501,984 A | * | 3/1996 | Hofstetter et al. | 436/518 |
| 5,860,711 A | * | 1/1999 | Kronberg et al. | 312/1 |
| 5,879,944 A | | 3/1999 | Komatsu | 436/50 |
| 6,001,309 A | | 12/1999 | Gamble et al. | 422/100 |
| 6,028,525 A | * | 2/2000 | Shukla et al. | 340/689 |
| 6,148,680 A | * | 11/2000 | Baeuerle et al. | 73/864.25 |
| 6,203,760 B1 | | 3/2001 | van der Plaats et al. | 422/104 |
| 6,349,654 B1 | * | 2/2002 | Peters | 108/26 |
| 6,637,476 B2 | | 10/2003 | Massaro | 141/237 |
| 6,866,820 B1 | * | 3/2005 | Otto et al. | 422/63 |
| 2002/0177788 A1 | * | 11/2002 | Hodges et al. | 600/583 |
| 2003/0077203 A1 | | 4/2003 | Gdmundsson et al. | 422/67 |
| 2003/0143123 A1 | * | 7/2003 | Maeda | 422/100 |
| 2003/0143748 A1 | | 7/2003 | Gudmundsson et al. | 436/43 |
| 2003/0143749 A1 | | 7/2003 | Gudmundsson et al. | 436/43 |
| 2003/0147778 A1 | | 8/2003 | Takahashi | 422/63 |
| 2003/0180188 A1 | | 9/2003 | Michael et al. | 422/99 |
| 2004/0018119 A1 | | 1/2004 | Massaro | 422/100 |
| 2004/0126283 A1 | | 7/2004 | Backes et al. | 422/104 |
| 2004/0146433 A1 | | 7/2004 | Massaro | 422/100 |

* cited by examiner

*Primary Examiner*—Robert Raevis
(74) *Attorney, Agent, or Firm*—Suiter Swantz pc llo

(57) ABSTRACT

The present invention is directed to an automated sampling and/or dispensing device for minimizing possible sample contamination from contaminants (e.g., mechanical pieces of machinery, dust, or the like) falling into sample vials during analysis by having no mechanical moving parts above stationary samples. The automated sampling or dispensing device may include a table for supporting a sample holder holding a sample vessel, a sample arm assembly extending for supporting a sample probe, the sample arm assembly including a z-axis support and a sample probe support arm, and a drive assembly couple to the z-axis support of the sample arm assembly for powering and positioning the sample arm assembly. The drive assembly causes the sample arm assembly to move in translation along the x-axis, in translation along an axis coaxial with the z-axis support, and radially about the z-axis for inserting the sample probe into the sample vessel.

26 Claims, 13 Drawing Sheets

AUTOMATED SAMPLING DEVICE

CROSS REFERENCE

The present application claims priority to U.S. Provisional Patent Ser. No. 60/604,548, entitled: Automated Sampling Device, filed on Aug. 26, 2004 which is hereby incorporated in its entirety.

FIELD OF INVENTION

The present invention relates generally to laboratory instrumentation, particularly automated sampling devices for drawing samples from stationary sample vessels, and more specifically, to an automated sampling device having a sample arm capable of three-axis movement with no mechanically wearing parts positioned above the stationary samples.

BACKGROUND OF THE INVENTION

In many laboratory settings, it is often necessary to analyze a large number of chemical or biochemical samples at one time. In order to stream-line such processes, the manipulation of samples has been mechanized. Such mechanized sampling is commonly referred to as autosampling and is performed using an automated sampling device or autosampler.

While a vast array of autosamplers are currently known and available, the majority of such devices share one common feature, employing robotic-like systems to analyze multiple vessels or containers containing samples in a given time. Many such devices are equipped with a robotic manipulator capable of two types of linear movement, i.e., x-y and vertical which allows the manipulator to access a container, transfer the container from a parent machine, and return the container to the appropriate position in the sample tray. Another common style of autosampler is one which employs robotic movement to move a sample probe above a sample vessel, or, alternatively, employs a moving table or conveyer to move the sample vessels underneath the sample probe.

Although autosamplers presently known in the art have greatly increased the ease and efficiency of assaying multiple samples at a given time, such samplers are disadvantageous in that they are likely to introduce an additional source for sample contamination, allowing for contamination of sample vessels by contaminants which may fall into containers during analysis. Present autosamplers employing mechanical parts which may cause dust, or the like, to fall into these containers because of mechanical wear of the devices that either is directly above the containers while they are moving or as the containers themselves move underneath a dispensing pipette. What is desired, therefore, is an automated sampling device without any mechanical moving parts positioned above stationary samples thereby removing such possible source of contamination.

SUMMARY OF INVENTION

Accordingly, the present invention is directed to an automated sampling device (autosampler) having no moving parts positioned above stationary samples being analyzed. As such, the automated sampling device eliminates possible sample contamination by contaminants (i.e. mechanical pieces of machinery, dust, lubricants, or the like) falling into the sample vessels during analysis from the automated sampling device.

In accordance with a first aspect of the present invention, an automated sampling or dispensing device is disclosed. In an exemplary embodiment, the automated sampling or dispensing device includes a support surface for supporting a sample holder suitable for holding a sample vessel. A sample arm assembly, including a z-axis support and a sample probe support arm, is included for supporting a sample probe. A drive assembly is coupled to the z-axis support of the sample arm assembly for powering and positioning the sample arm assembly. The drive assembly is preferably capable of causing the sample arm assembly to move in translation along the x-axis, in translation along an axis coaxial with the z-axis support, and radially about the z-axis for inserting the sample probe into the sample vessel and removing the sample probe from the sample vessel.

In accordance with a second aspect of the present invention, an automated sampling or dispensing device is disclosed. In an exemplary embodiment, the automated sampling or dispensing device includes a support surface for supporting a sample holder suitable for holding a sample vessel, the support surface having a center slot formed longitudinally therein. A drive assembly is mounted to the support surface for providing power to the automated sampling device. The sample arm assembly is attached to the drive assembly for supporting a sample probe and includes a z-axis support and a sample probe support arm. Preferably, the arm length of the sample arm assembly is no more than one-half the length of a linear translation of the center slot. Such configuration allows nearly one hundred percent of the footprint to be accessed by the sample probe.

In accordance with a third aspect of the present invention, an automated sampling or dispensing device is disclosed. As illustrated in an exemplary embodiment, the automated sampling or dispensing device includes a sample arm assembly for supporting a sample probe wherein the sample arm assembly includes a z-axis support and a sample probe support arm. A drive assembly is coupled to the z-axis support of the sample arm assembly for powering and positioning the sample arm assembly. A support surface for supporting a sample holder holding a sample vessel is also included wherein the support surface is mounted on wheels. The use of wheels facilitates the preparation of samples at a location separate from the analytical instruments.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles of the invention.

BRIEF DESCRIPTION OF DRAWINGS

The numerous objects and advantages of the present invention may be better understood by those skilled in the art by reference to the accompanying figures in which.

DETAILED DESCRIPTION OF INVENTION

Reference will now be made in detail to the presently preferred embodiments of the invention, examples of which are illustrated in the accompanying drawings.

Figure 1:
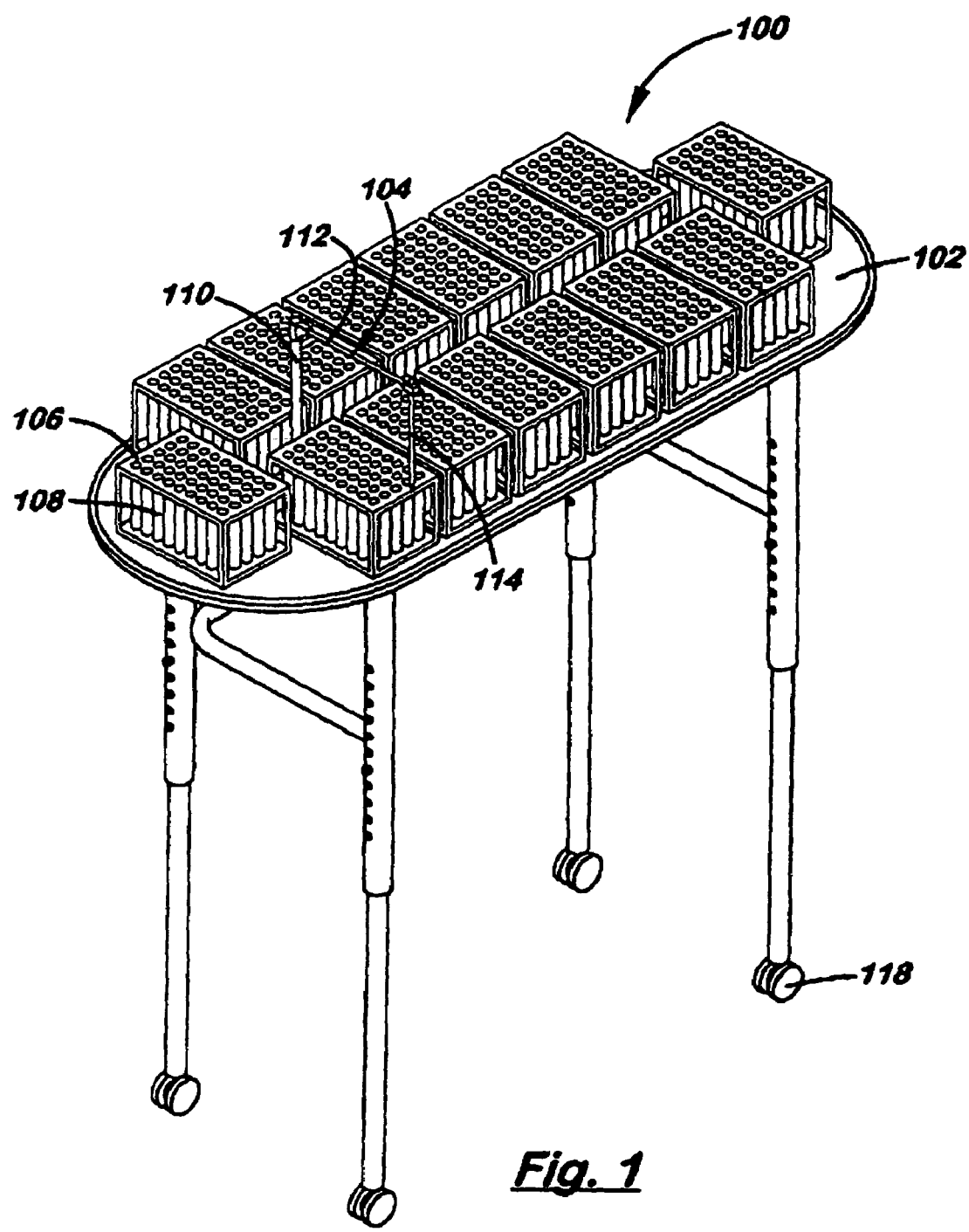
FIG. 1 is an isometric view illustrating an automated sampling or dispensing device in accordance with an exemplary embodiment of the present invention.

FIG. 1 illustrates automated sampling device 100 in accordance with an exemplary embodiment of the present invention. Automated sampling device 100 includes table top 102 and sample arm assembly 104. Further, sample holders 106 holding multiple sample vessels 108 are present on table top 102 in preparation for sample assaying. It should be understood that automated sampling device 100 may assay from one to many hundreds of samples (e.g., greater than 1200 samples in the exemplary embodiment illustrated) in a given time depending upon test requirements.

In the embodiment illustrated, sample arm assembly 104 includes a z-axis support 110 and a sample probe support arm 112 that supports a sample probe 114. As illustrated, the z-axis which is aligned with gravity or vertical axis. In use, sample probe 114 is mounted to sample probe support arm 112 which is moved through space in three dimensions, or about an axis having y-motion that is a substantially rotary motion and along an axis having x-motion which is at least substantially horizontal linear motion or translation, and along a z-axis that is at least substantially vertical, for linear motion or translation. In an embodiment, the length of a sample probe support arm (the length of arm extending from the y-rotary axis) is no more than one-half the length of a linear translation of the center slot (i.e. is no more than half of the length of x-axis linear motion). In a preferred embodiment, the length of the sample probe support arm is approximately equal to one-half the length of a linear translation of the center slot. Such configuration allows nearly one hundred percent of the footprint of the table to be accessed by the sample probe. Footprint is defined as being substantially equivalent to an area encompassed by the area of the table top. In an additional embodiment, the y-rotary axis of an automated sampling device allows for access to sample vessels on either side of the x-axis motion of linear travel (i.e. on either side of the center slot).

In an embodiment, the components of sample arm assembly 104 are formed of carbon composite materials. Further, all exposed surfaces of the sample arm assembly 104 are made from inert or fluoropolymer-covered materials (i.e. Teflon®). It should be understood, however, that the sample arm assembly may be made with any suitable material known in the art, including aluminum, steel, plastic, and the like.

In addition, sample arm assembly 104 is designed to attach to any type of surface support including a table top. Such assembly may be attached to either side of the center slot. In an embodiment, table top 102 may be mounted onto legs with casters 118, rollers and the like. Such configuration increases the mobility of the automated sampling device, thereby facilitating preparation of samples at a location separate from the analytical instruments. Further, this configuration provides storage room underneath the table top which may be absent with bench-top automated sampling devices. The height of the table is adjustable to compensate for the effects of gravity on liquid flow rates when self-aspirating sampling devices are utilized. The ability to adjust table top height also allows the automated sampling device to accommodate various sized sample vessels.

Figure 2A:
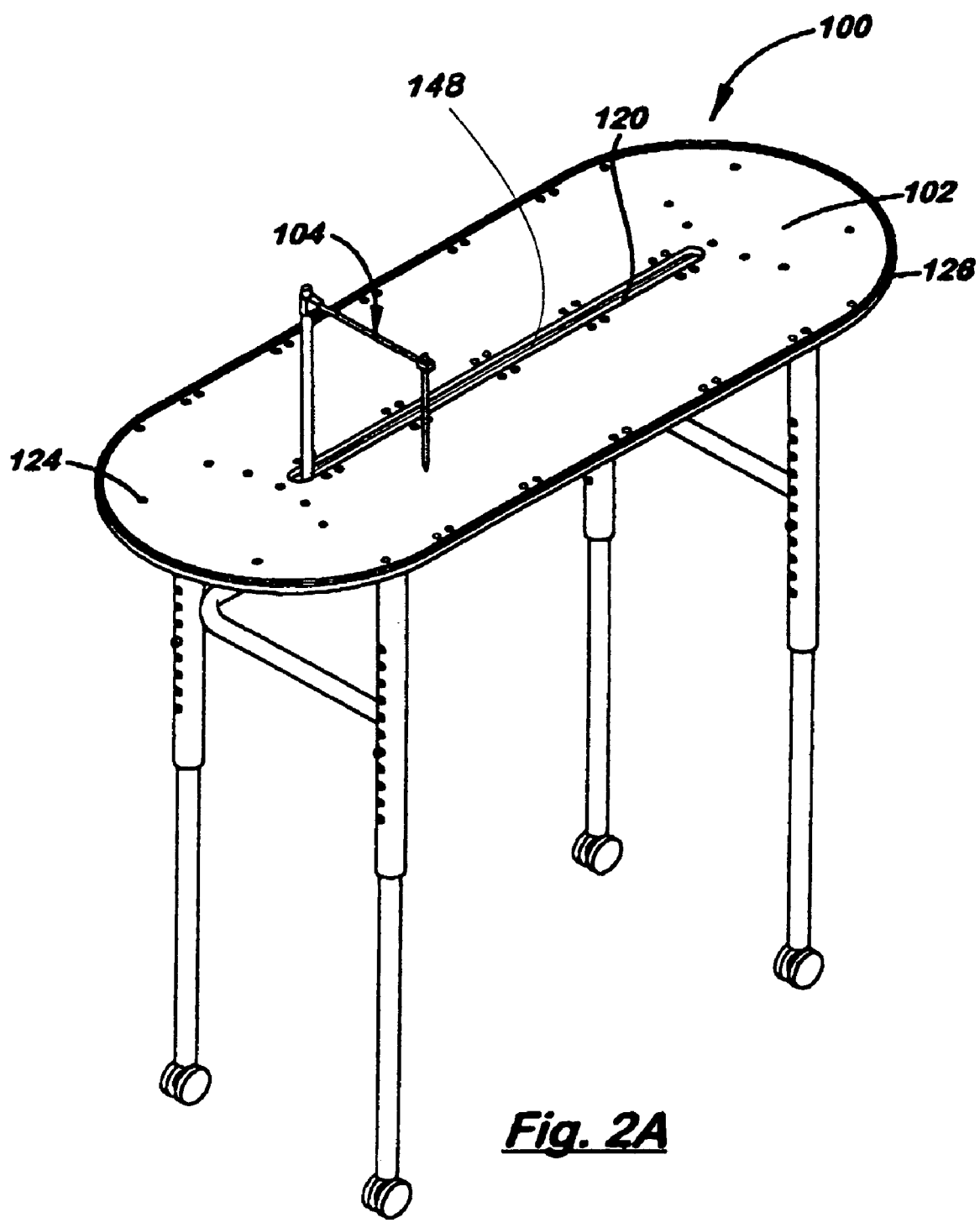
FIG. 2A is a partial isometric view of an automated sampling or dispensing device, wherein a center slot in the support surface is present allowing the sample arm assembly to be connected with the drive assembly.
Figure 2B:
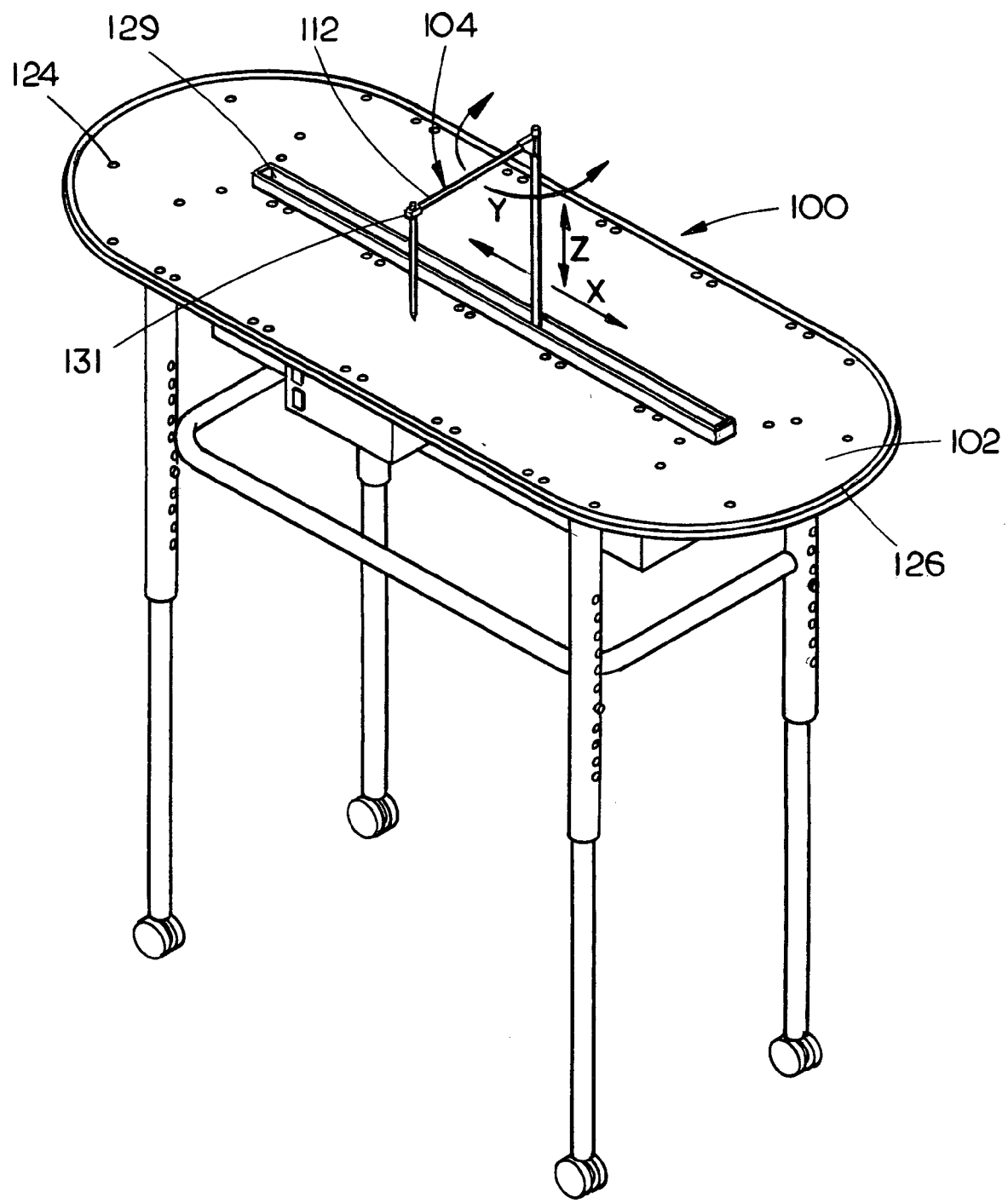
FIG. 2B is a partial isometric view of an automated sampling or dispensing device, wherein a raised slot on the support surface is present to attach the sample arm assembly to the drive assembly.

FIGS. 2A and 2B are additional illustrations of automated sampling or dispensing devices in which the sample arm assembly is attached to the drive assembly via a center slot or a raised slot, respectively. In FIG. 2A, automated sampling device 100 is comprised of sample arm assembly 104 extending through center slot 120 and table top 102 including a plurality of recesses 124 and the channel 126. The sample arm assembly 104 is attached to the drive assembly (not shown) via center slot 120. In an embodiment, the plurality of recesses is coupled with sensors for detecting the location of sample holders. The sample holder location information may then be transferred to a controller of a drive assembly controlling the sample arm assembly providing the alignment system. The previous configuration allows the sample arm assembly to detect the location of sample vessels on the table top at a given time. Channel 126 runs along the edge of table top 102 to collect possible sample spillage. The center slot 120 may include a ribbon to deflect spills away from the drive assembly. For example in, an embodiment as illustrated in FIG. 2A a ribbon 148 of fluoropolymer inert material is placed on the same side of the center slot 120 as that which includes the drive assembly. Such configuration will deflect fluid to the opposite side of the slot thereby preventing the fluid from contacting the drive assembly.

In addition to FIG. 2A, FIG. 2B demonstrates an automated sampling or dispensing device including a sample arm assembly 104 attached to the drive assembly 128 via a raised slot 129. In one embodiment, a magnet 131 is attached to the end of the sample probe support arm 112 which allows detection of a three-dimensional position in space wherein the magnet 131 is embedded into the sample probe support arm 112 and is detected by a sensing means such as a Hall Effect sensor.

Figure 3:
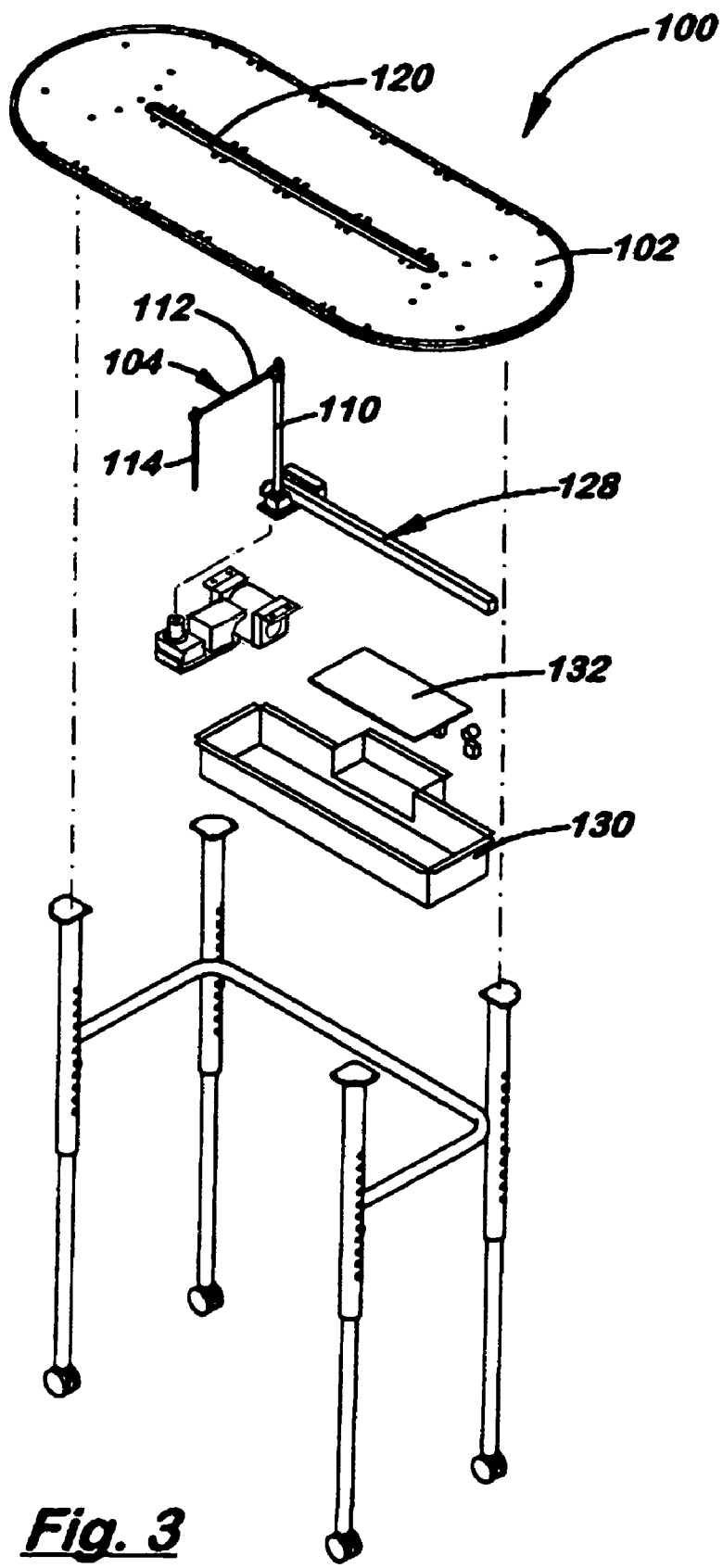
FIG. 3 is an exploded view of the automated sampling or dispensing device shown in FIG. 1, further illustrating components of the device.

Referring now to FIG. 3, an exploded view of the components comprising the automated sampling device 100 is provided. The automated sampling device 100 is comprised of a table top 102 with center slot 120, drive assembly 128, sample arm assembly 104, housing 130, and controller 132. Sample arm assembly 104 includes z-axis support 110 attached to drive assembly 128, sample probe support arm 112 attached to z-axis support 110, and sample probe 114 attached to sample probe support arm 112. Sample arm assembly 104 is controlled by drive assembly 128 and controller 132. In an embodiment, drive assembly 128 causes sample arm assembly 104 to move along center slot 120, in translation along an axis coaxial to z-axis support 110, and radially about the z-axis for inserting sample probe 114 into a sample vessel. Further, sample arm assembly 104 is no more than one-half the length of a linear translation of the length of center slot 120. As previously mentioned, such configuration allows nearly one hundred percent of the footprint to be accessed by sample probe 114. In addition, automated sampling device 100 is capable of assaying hundreds of samples at a given time without any operator assistance, thereby allowing the operator to perform other tasks. Moreover, it is possible to set-up the automated sampling device to assay samples overnight, allowing work productivity to be increased.

To accommodate gross differences in sample vessel height, sample probe support arm 112 may be moved up or down z-axis support 110 as desired prior to sample assaying. Once the desired position is reached, sample probe support arm 112 is secured into a fixed position on z-axis support 110 and sample vessels containing samples may be loaded onto the table top. This feature allows the automated sampling device to be used on various sizes of sample vessels while still not having any mechanical moving parts above stationary samples. Additionally, housing 130 encloses drive assembly 128 to protect the assembly from debris, dust, contaminates, and the like. Housing 130 may be made of any suitable material, e.g. blow molded polyethylene.

Figure 4A:
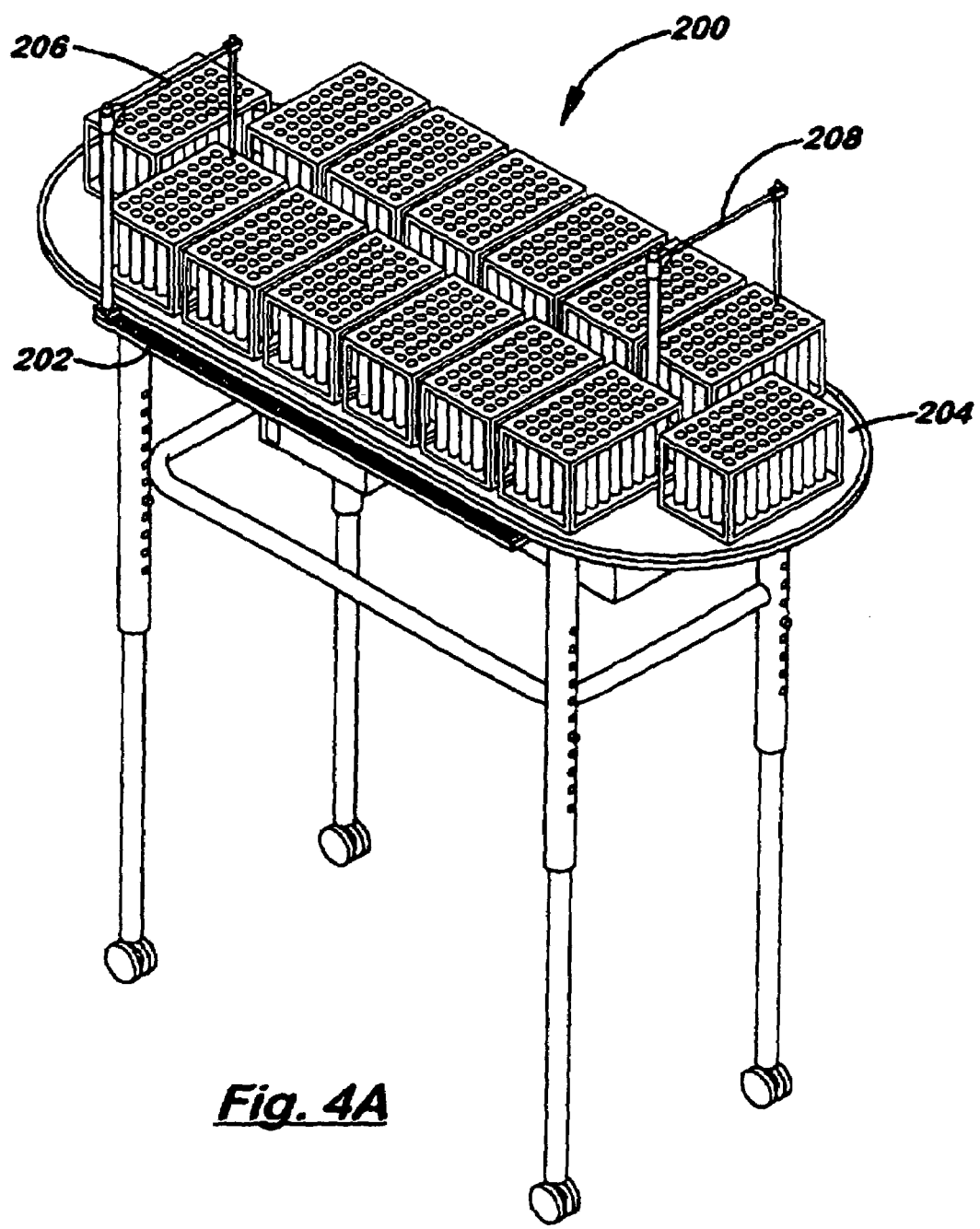
FIG. 4A is an isometric view illustrating an automated sampling or dispensing device in accordance with a second exemplary embodiment of the present invention wherein multiple sampling arm assemblies and drive assemblies are mounted to the top of the support surface of the automated sampling or dispensing device.
Figure 4B:
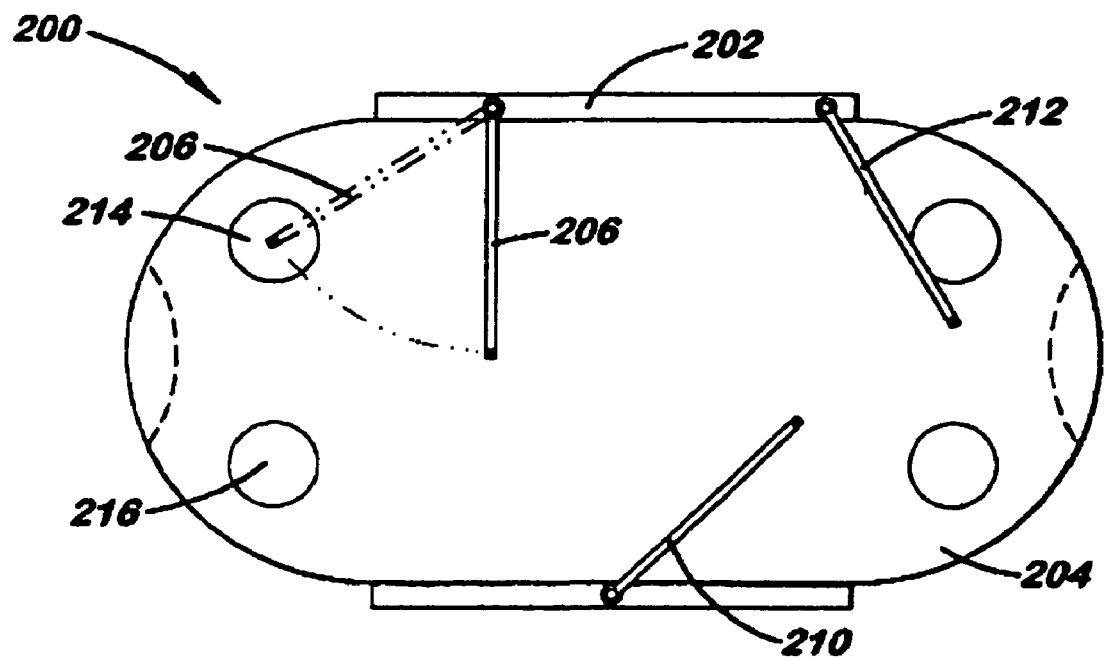
FIG. 4B is plan view illustrating an automated sampling or dispensing device in accordance with the second exemplary embodiment of the present invention, wherein multiple sample arm assemblies and rinse stations are present on one support surface.

FIGS. 4A and 4B illustrate an automated sampling device 200 in accordance with a second exemplary embodiment of the present invention wherein multiple sampling arm assemblies (i.e. sample arm assembly 206, 208, and 210) are mounted to the table top of the automated sampling device. Automated sampling device 200 includes multiple automated sampling devices attached to a table top at one time. A rail 202 is attached to the edge of table top 204 to enable the attachment of additional sample arm assemblies (i.e. sample arm assembly 206 and 212). Utilization of additional sample arm assemblies allows multiple sample zones to be set up (i.e. prep zone, assaying zone, and the like).

In additional embodiments, various types of multiple rinse or eluent stations may be included in the automated sampling device. For instance, multiple rinse stations (i.e. 214 and 216) of the overflow type designed to reduce the chance of carry-over contamination may be present. Further, overflow rinse stations may contain a series of different chemical rinses to reduce contamination between sample analyses (e.g. surfactant, nitric acid, hydrofluoric acid, and deionized water). For multiple eluent stations, the automated sampling device may contain such stations for step elution from a chromatographic column.

Figure 5:
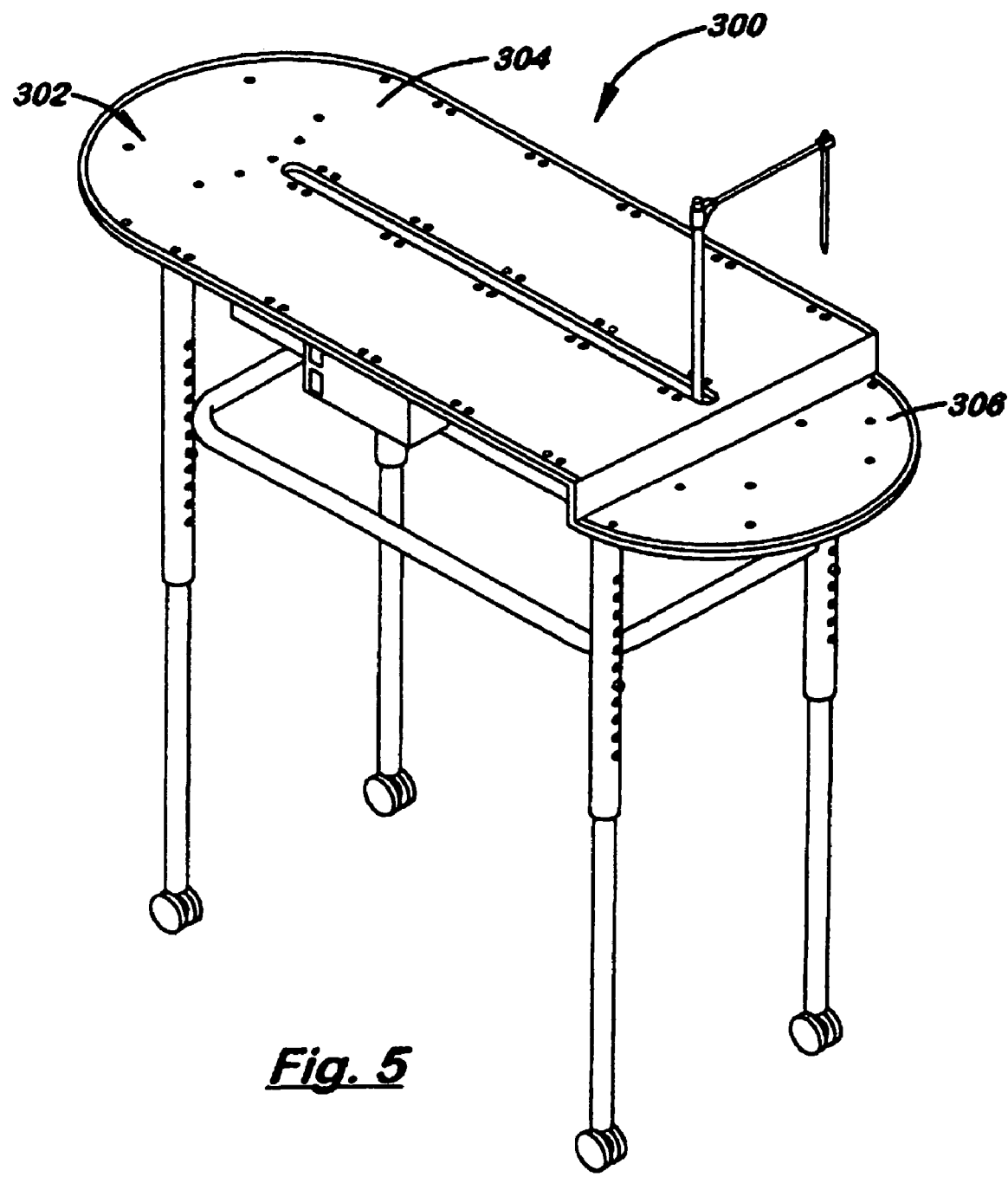
FIG. 5 is an isometric view illustrating an automated sampling or dispensing device in accordance with a third exemplary embodiment of the present invention, wherein the support surface of the automatic sampling or dispensing device is provided with more than one plane.

Referring now to FIG. 5, an automated sampling device in accordance with a third exemplary embodiment of the present invention is disclosed wherein a table top having more than one plane is provided. Automated sampling device 300 includes table top 302 which has more than one plane, plane one 304 and plane two 306. Such configuration allows table top 302 to accommodate various sizes of vessels. For instance, the height of vessels in plane two 306 may be taller than vessels in plane one 304 of table top 302.

Figure 6:
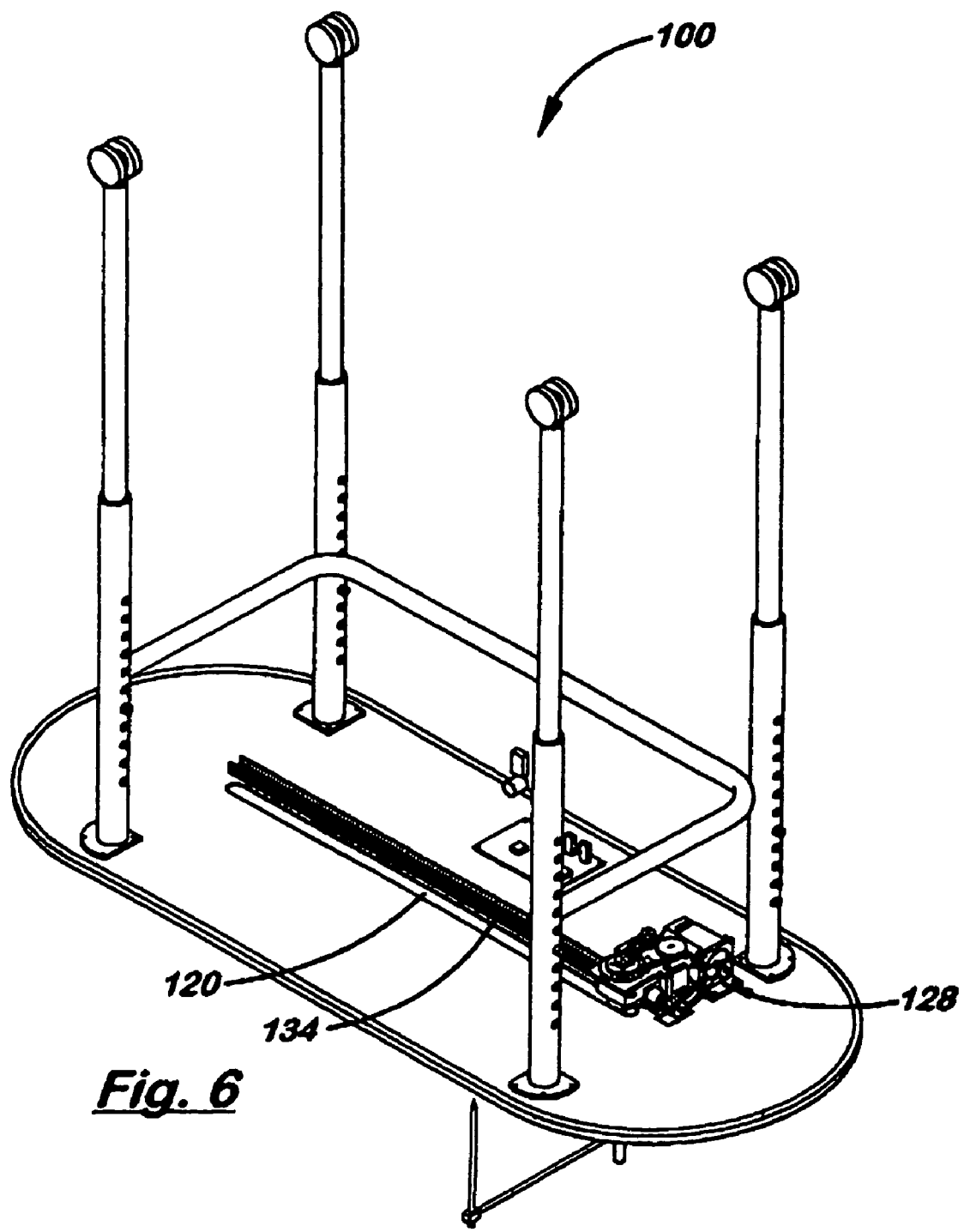
FIG. 6 is an isometric view of the automated sampling or dispensing device shown in FIG. 1, further illustrating the drive assembly.
Figure 7:
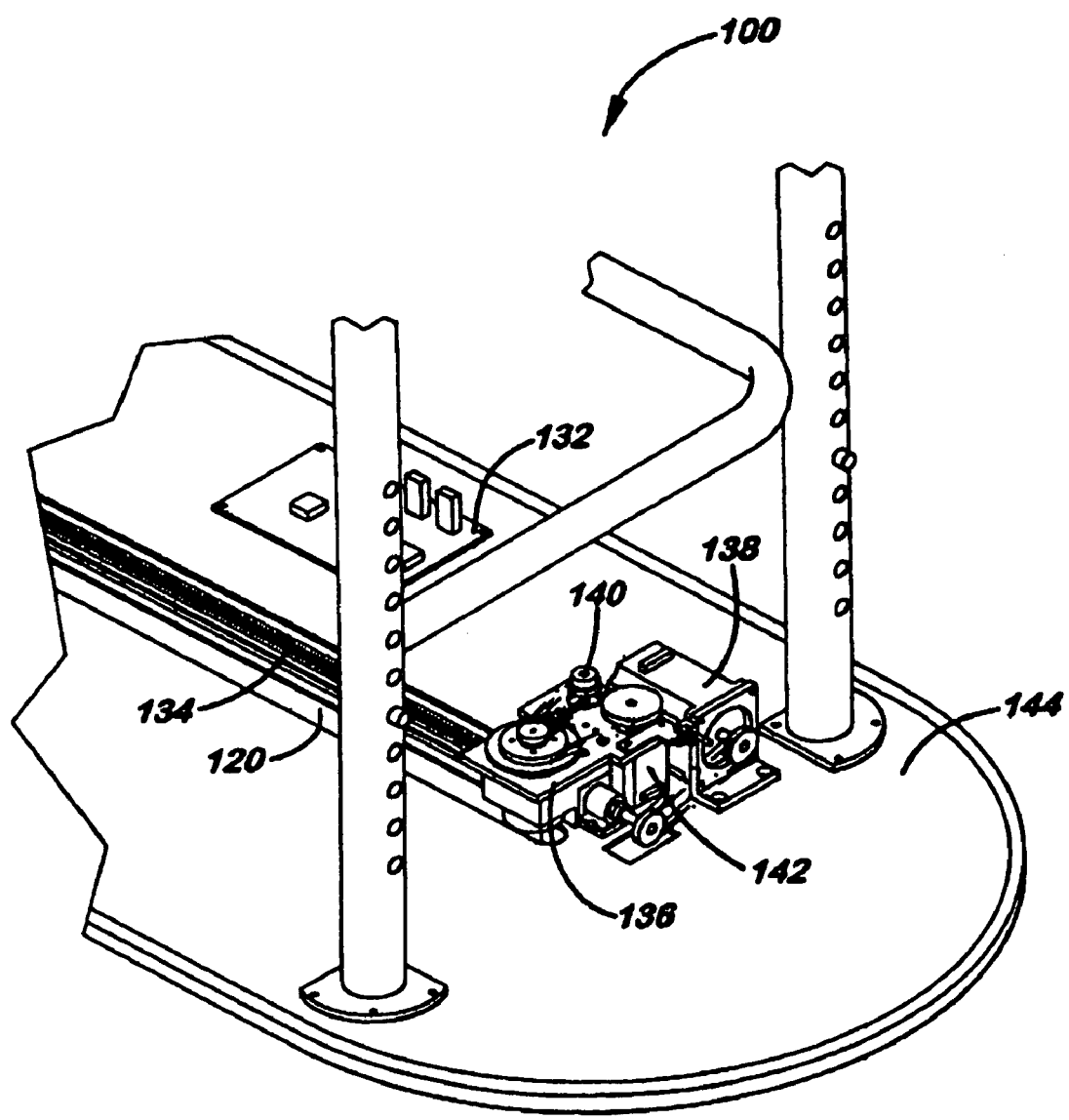
FIG. 7 is a partial isometric view of the drive assembly shown in FIG. 6, further illustrating components of the drive assembly.

FIGS. 6 and 7 further illustrate a drive assembly of automated sampling device 100 attached to a table top bottom. First, FIG. 6 provides an overview of a drive assembly in accordance with the present invention depicting a linear drive 134 running parallel to center slot 120 and connected to sled 128. FIG. 7 is an enlarged view of the drive assembly illustrated in FIG. 6. Drive assembly 100 is comprised of motor one 138, motor two 140, motor three 142, sled 136, linear drive 134, and controller 132. Motor one 138 controls translation of a sample arm assembly's movements along the center slot 120 and is attached to table top bottom 144 and linear drive 134. Any conventional stepper motor known in the art may be used to control translation of the sample arm assembly's movements along center slot 120. Moreover, those of skill in the art will appreciate that any suitable linear drive may be used including a worm drive. Motor two 140 controls angular rotation of a sample arm assembly and is connected to sled 136. In an embodiment, motor two 140 is a radial motor. Motor three 142 controls vertical movement of a sample arm assembly and is attached to sled 136. Any suitable stepper motor may be used for controlling vertical movement of the sample arm assembly. In an additional embodiment, motor three 142 is a slip-clutch system. Further, in accordance with the present invention, the drive assembly may be hard-wired or in the preferred embodiment, controlled via wireless communications. Thus, wireless communications may be utilized to connect controller 132 with the desired analytical instrument (not shown). Utilization of wireless communications allows sample assaying to occur without requiring physical connection with a controller computer increasing mobility of the automated sampling device.

Figure 8:
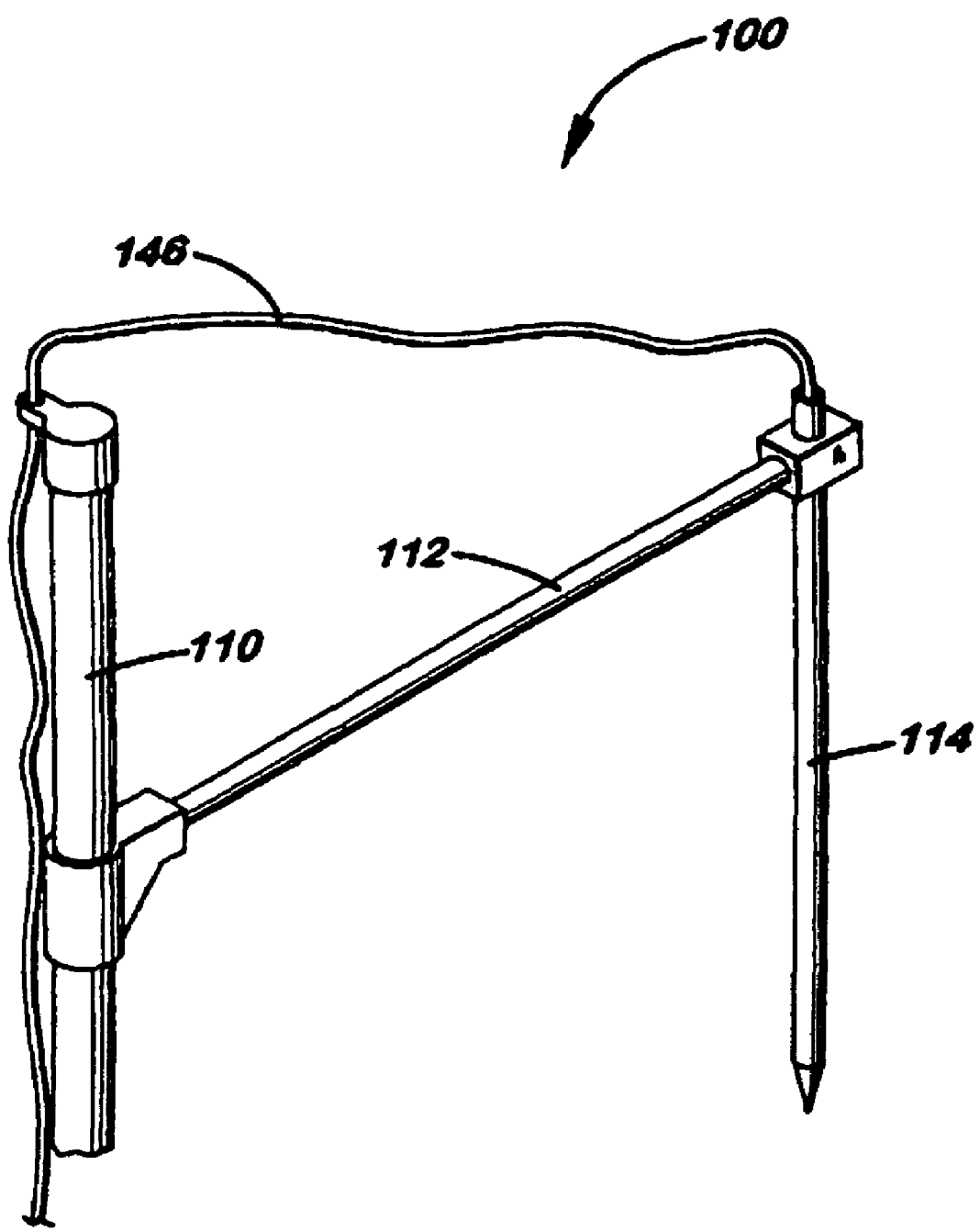
FIG. 8 is a partial isometric view of a sample arm assembly for an automated sampling or dispensing device in accordance with an exemplary embodiment of the present invention.

FIG. 8 provides a detailed depiction of a sample arm assembly of an automated sampling device in accordance with the first exemplary embodiment of the present invention. As previously described, the sample arm assembly includes z-axis support 110 attached to a drive assembly (see FIGS. 6 and 7), sample probe support arm 112 attached to z-axis support 110, and sample probe 114 attached to sample probe support arm 112. In an embodiment, the sample arm assembly is attached to the drive assembly via the z-axis support extending through a center slot in the table top; in such embodiment, the drive assembly is attached to a table top bottom. However, it should be understood to those skilled in the art that the drive assembly may be disposed in a variety of locations including on top of the table top without departing from the scope of the present invention.

In an additional embodiment in accordance with the present invention, sample tubing 146 is present to allow sample removal or reagent delivery as desired. Further, a slip bearing is built into sample probe 114 to prevent winding of sample tubing 146. It is contemplated that the sample may be delivered to various types of scientific instrumentation (e.g. inductively couple plasma system, mass spectrometer) or a number of other types of vessels (e.g. waste collecting bucket following a wash step). It is further contemplated that the sample tubing may be flexible (as shown) or rigid, comprised of plastic, metal, and the like without departing from the scope and spirit of the present invention. In another embodiment, the automated sampling device may be equipped with one or more independent components for the purpose of sample preparation, sample dilution, addition of standards to samples or sample acidification.

Figure 9A:
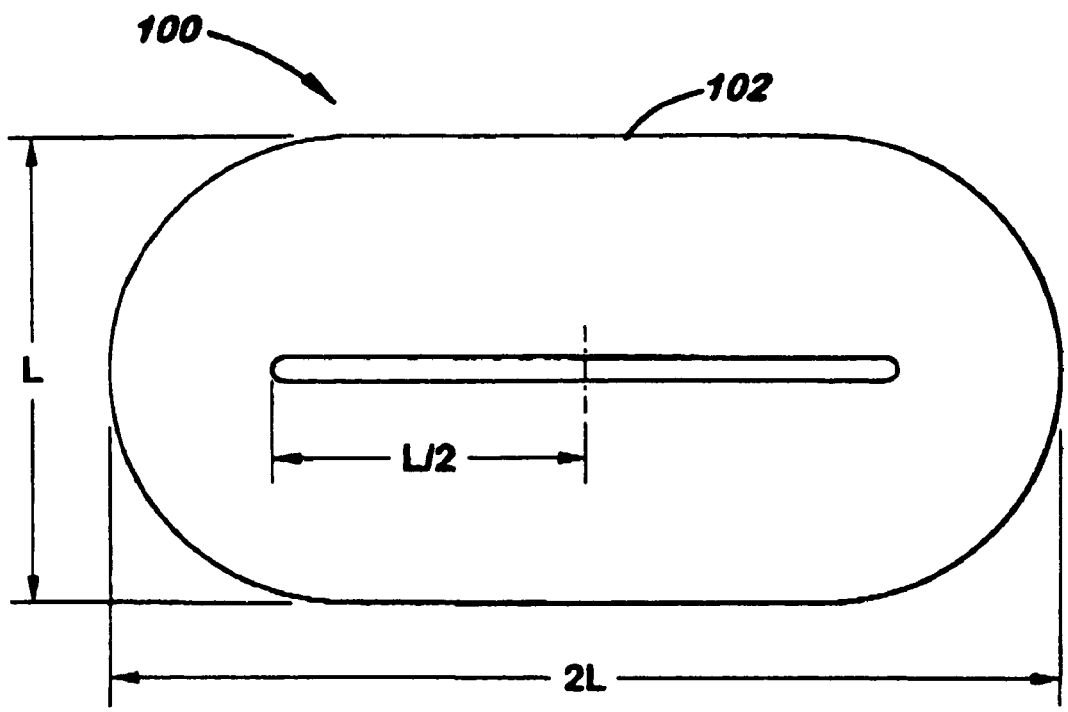
FIG. 9A is plan view illustrating a support surface for use with an automated sampling or dispensing device, wherein the support surface includes a slot and has a footprint in accordance with the first exemplary embodiment of the present invention.
Figure 9B:
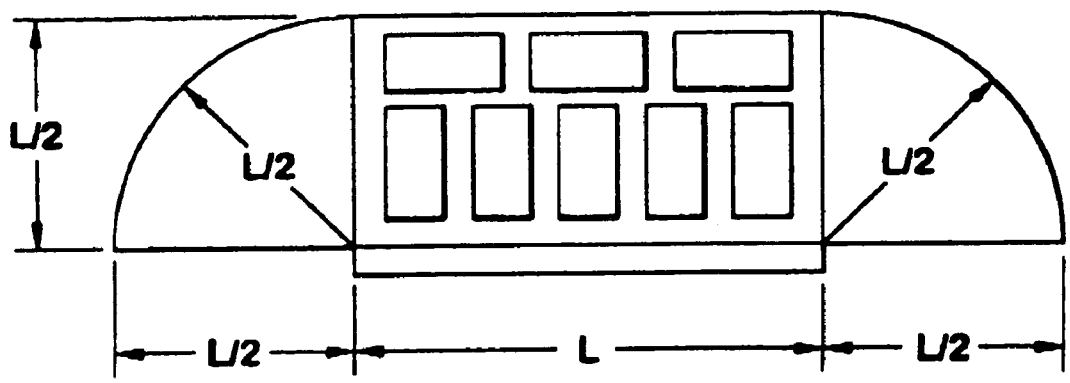
FIG. 9B is plan view illustrating a support surface for use with an automated sampling or dispensing device, in accordance with a fourth exemplary embodiment of the present invention.

Referring to FIGS. 9A and 9B, tables for use with an automated sampling device are described in accordance with exemplary embodiments of the present invention. First, the table 102 includes a slot of length l providing for translation of the sample arm assembly along the length of the table. Further, the table 102 has a footprint for maximizing the usable area of the table 102. As illustrated in FIG. 9A, preferably, the table 102 has a width l substantially equal to the length of the slot l. Moreover, the table 102 is twice as long as the slot, having a length of 2l. Further, the arm length of a sample probe assembly (as shown in FIGS. 1, 2, and 3) is half the length of the slot, having length l/2. This configuration allows for approximately one hundred percent of the footprint of the table to be accessed. In contrast, FIG. 9B illustrates an additional embodiment in accordance with the present invention whereby the table is the shape of a semi-circle and a non-centered slot system is employed.

Figure 10:
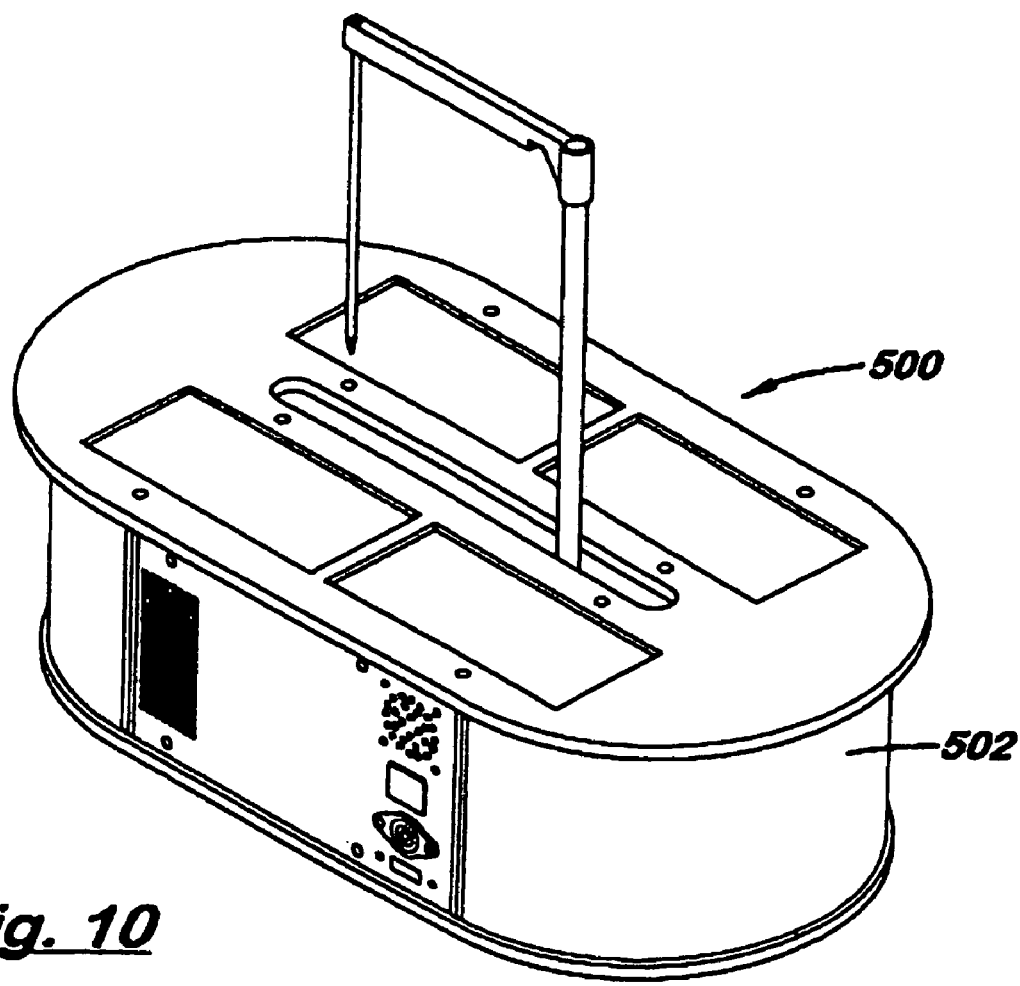
FIG. 10 is an isometric drawing of an automated sampling or dispensing device in accordance with a fifth exemplary embodiment of the present invention, wherein the device includes a shroud.

Referring to FIG. 10, automated sampling or dispensing device 500 includes a shroud 502. In an exemplary embodiment, the shroud 502 substantially encloses the drive assembly 128 (FIG. 3) for protecting the drive assembly from dust and debris, or preventing dust and debris from the drive assembly from contaminating samples during assaying.

Figure 11:
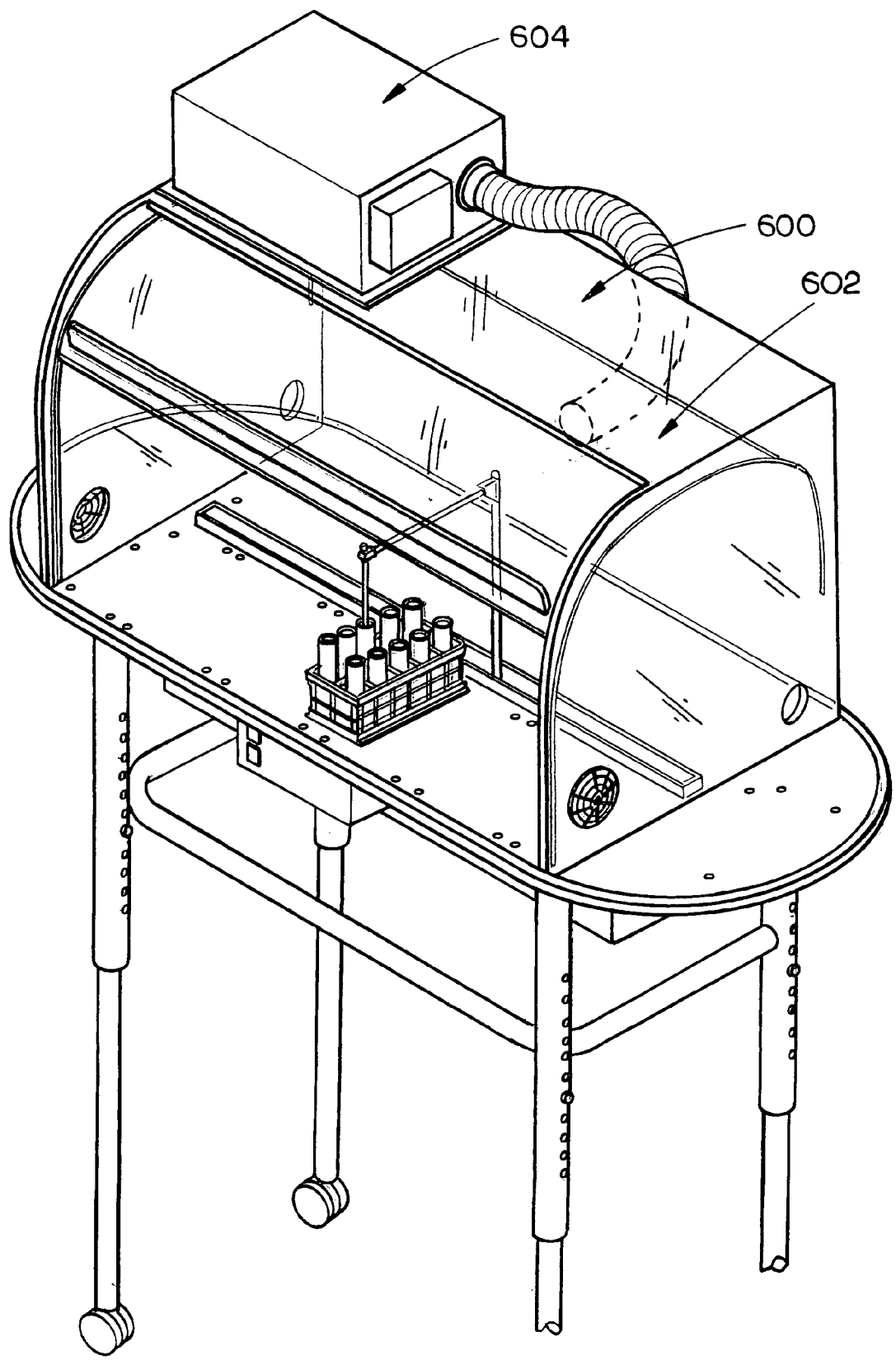
FIG. 11 is an isometric drawing of an automated sampling or dispensing device in accordance with a sixth exemplary embodiment of the present invention, wherein the device is contained within a hood.

FIG. 11 illustrates automated sampling device 600 completely enclosed within a hood 602. Use of the hood allows the operations inside the hood to be isolated from the outside environment. The area within the hood may be ventilated to prevent the entry of contaminates such as bacteria or airborne substances. In one specific embodiment, the air drawn into the enclosure is passed through a high efficiency particulate air (HEPA) filter. Further, processing of samples which contain hazardous chemicals within a hood allows such samples to be processed without further exposing the user to such chemicals during processing.

It is believed that the present invention and many of its attendant advantages will be understood by the foregoing description. It is also believed that it will be apparent that various changes may be made in size, materials, shape, form, function, manner of operation, assembly and use of the components thereof without departing from the scope and spirit of the invention or without sacrificing all of its material advantages. The form herein before described being merely an explanatory embodiment thereof. Further, it is contemplated that the specific order or hierarchy of steps in the method can be rearranged while remaining within the scope and spirit of the present invention. It is the intention of the following claims to encompass and include such changes.

What is claimed is:

1. An automated sampling or dispensing device, comprising:
   a support surface for supporting a sample holder, the sample holder being suitable for holding a sample vessel;
   a sample arm assembly for supporting a sample probe, the sample arm assembly including a z-axis support comprising a vertically disposed member that is generally perpendicular to the support surface and a sample probe support arm mounted to the vertically disposed member for supporting the sample probe; and
   a drive assembly coupled to the z-axis support of the sample arm assembly for powering and positioning the sample arm assembly,
   wherein the drive assembly causes the sample arm assembly to move in translation along an axis parallel to the support surface and causes the sample probe support arm to move in translation along an axis coaxial with the vertically disposed member and to rotate about the axis coaxial with the vertically disposed member.

2. The automated sampling or dispensing device of claim 1, wherein the support surface is comprised of a table.

3. The automated sampling or dispensing device of claim 2, wherein the table is comprised of a center slot and the sample arm assembly is attached to the drive assembly by the z-axis support extending through the center slot, the drive assembly being attached to the bottom of the table.

4. The automated sampling or dispensing device of claim 2, wherein the table is at least two times as wide as the arm length of the sample probe support arm and four times as long as the length of the sample probe support arm.

5. The automated sampling or dispensing device of claim 3, wherein the table is at least as wide as the length of the center slot and twice as long as the length of the center slot.

6. The automated sampling or dispensing device of claim 2, wherein the arm length of the sample arm assembly is no more than one-half the length of possible drive assembly linear translation along the x-axis.

7. The automated sampling or dispensing device of claim 1, wherein the support surface is mounted on wheels.

8. The automated sampling or dispensing device of claim 1, wherein the drive assembly is comprised of a controller, a linear drive, and a sled, a first motor for controlling translation of the sample arm assembly movements along the axis parallel to the support surface and is attached to the support surface and the linear drive, a second motor for controlling angular rotation of the sample arm assembly and is connected to the sled, and a third motor for controlling movement along the z-axis of the sample arm assembly and is attached to the sled.

9. The automated sampling or dispensing device of claim 1, wherein the sample arm assembly and the sample probe are comprised of carbon fiber material.

10. The automated sampling or dispensing device of claim 9, wherein the carbon fiber material is coated with a fluoropolymer inert material.

11. The automated sampling or dispensing device of claim 1, wherein the drive assembly is below the level of the support surface.

12. The automated sampling or dispensing device of claim 1, wherein the drive assembly includes at least one of wireless transmitter or receiver for communicating with a controller computer.

13. The automated sampling or dispensing device of claim 1, further comprising a suction system attached to the sample arm assembly allowing sample to be removed from the sample vessel.

14. The automated sampling or dispensing device of claim 1, further comprising a dispensing system attached to the sample arm assembly allowing a reagent to be dispensed into the sample vessel.

15. The automated sampling or dispensing device of claim 1, further comprising a rail attached to an edge of the support surface for supporting the sample arm assembly.

16. The automated sampling or dispensing device of claim 15, further comprising rinse stations for rinsing the sample probe.

17. The automated sampling or dispensing device of claim 1, further comprising an alignment system for aligning sample holders to the support surface.

18. The automated sampling or dispensing device of claim 1, further comprising a device placed on the end of the sample probe support arm that allows detection of three dimensional position in space.

19. The automated sampling or dispensing device of claim 18, wherein the device includes a magnet embedded into the end of the sample probe support arm.

20. The automated sampling or dispensing device of claim 1, wherein the drive assembly is enclosed by a housing is configured to protect the drive assembly from dust/debris.

21. The automated sampling or dispensing device of claim 1, wherein the support surface includes a channel along the periphery of the support surface for collecting potential spillage.

22. The automated sampling or dispensing device of claim 1, wherein the support surface is an adjustable table.

23. An automated sampling or dispensing device, comprising:
   a sample arm assembly for supporting a sample probe, the sample arm assembly including a z-axis support comprising a vertically disposed member that is generally perpendicular to the support surface and a sample probe support arm mounted to the vertically disposed member for supporting the sample probe; and
   a drive assembly coupled to the z-axis support of the sample arm assembly for powering and positioning the sample arm assembly; and
   a support surface for supporting a sample holder suitable for holding a sample vessel and a clean environment enclosure,
   wherein the drive assembly causes the sample arm assembly to move in translation along an axis parallel to the support surface and causes the sample probe support arm to move in translation along an axis coaxial with the vertically disposed member and to rotate about the axis coaxial with the vertically disposed member.

24. The automated sampling or dispensing device of claim 23, wherein the drive assembly is located outside of the clean environment enclosure.

25. The automated sampling or dispensing device of claim 24, wherein the device includes wheels for transporting the device, the wheels being attached to the support surface by support members.

26. The automated sampling or dispensing device of claim 25, further comprising a filtering system coupled to the clean environment enclosure for maintaining sample environment purity during transport.

* * * * *